US009494538B2

(12) United States Patent
Kozicki et al.

(10) Patent No.: US 9,494,538 B2
(45) Date of Patent: Nov. 15, 2016

(54) AGRICULTURAL MOISTURE SENSOR WITH CO-PLANAR ELECTRODES

(71) Applicant: Deere & Company, Moline, IL (US)

(72) Inventors: Andrze J Kozicki, Milan, IL (US); Michael Tuchscherer, West Fargo, ND (US); Michael L. Rhodes, Richfield, MN (US); Jefrey S. Wigdahl, Ames, IA (US); James J. Phelan, Bettendorf, IA (US); Brian J. Booth, Fargo, ND (US); Jerry B. Hall, Johnston, IA (US)

(73) Assignee: Deere & Company, Moline, IL (US)

( * ) Notice: Subject to any disclaimer, the term of this patent is extended or adjusted under 35 U.S.C. 154(b) by 213 days.

(21) Appl. No.: 14/245,069

(22) Filed: Apr. 4, 2014

(65) Prior Publication Data
US 2015/0285752 A1   Oct. 8, 2015

(51) Int. Cl.
| | | |
|---|---|---|
| *G01R 27/28* | (2006.01) | |
| *G01N 27/02* | (2006.01) | |
| *G01D 5/24* | (2006.01) | |
| *A01D 41/12* | (2006.01) | |
| *A01F 12/46* | (2006.01) | |

(Continued)

(52) U.S. Cl.
CPC ............ *G01N 27/02* (2013.01); *A01D 41/1243* (2013.01); *A01F 12/46* (2013.01); *A01F 17/00* (2013.01); *B65G 43/00* (2013.01); *G01D 5/24* (2013.01); *G01D 5/241* (2013.01); *G01N 27/223* (2013.01); *G01D 5/2412* (2013.01); *G01D 5/2417* (2013.01)

(58) Field of Classification Search
CPC .............. G01R 27/02; G01R 27/2605; G01R 19/0092; G01R 27/00; G01R 27/26; G01D 5/24; G01D 5/241; G01D 5/2412; G01D 5/2417

USPC .......... 324/76.11–76.83, 459, 600, 649, 519, 324/634, 640, 643, 644, 658, 660, 661, 662, 324/663, 664, 671, 686, 688, 689, 691, 693, 324/694, 695, 699, 701, 750.17; 702/47, 702/52, 85, 97, 127, 155, 158; 73/24.04, 73/25.04, 29.01, 73, 74
See application file for complete search history.

(56) References Cited

U.S. PATENT DOCUMENTS

| 3,491,292 A | 1/1970 | Evans |
| 3,826,979 A | 7/1974 | Steinmann |

(Continued)

FOREIGN PATENT DOCUMENTS

DE        19610599 A1    8/1997

OTHER PUBLICATIONS

European Search Report issued in counterpart application No. 15160069.9, dated Sep. 9, 2015 (8 pages).

(Continued)

*Primary Examiner* — Son Le
*Assistant Examiner* — Raul Rios Russo
(74) *Attorney, Agent, or Firm* — Joseph R. Kelly; Kelly, Holt & Christenson, PLLC

(57) ABSTRACT

A moisture sensor that has a drive electrode and a separate sense electrode is described. Both electrodes have surfaces that face the sensed material and the surfaces are co-planar. The drive electrode receives an excitation signal and generates an electric field that produces a current in the sense electrode. The current is indicative of moisture in the sensed material.

23 Claims, 5 Drawing Sheets

(51) Int. Cl.
*A01F 17/00* (2006.01)
*B65G 43/00* (2006.01)
*G01N 27/22* (2006.01)
*G01R 27/26* (2006.01)
*G01D 5/241* (2006.01)

(56) References Cited

U.S. PATENT DOCUMENTS

| | | | |
|---|---|---|---|
| 6,388,453 | B1 | 5/2002 | Greer |
| 6,686,749 | B2 | 2/2004 | Rains et al. |
| 6,917,206 | B2 | 7/2005 | Rains et al. |
| 6,982,562 | B2 | 1/2006 | Rains et al. |
| 2003/0080753 | A1 | 5/2003 | Rains et al. |
| 2005/0156608 | A1 | 7/2005 | Katz |
| 2008/0245582 | A1* | 10/2008 | Bytheway ............... G06F 3/044 178/18.06 |
| 2008/0246496 | A1* | 10/2008 | Hristov ................. G06F 3/044 324/686 |
| 2010/0321043 | A1* | 12/2010 | Philipp ................. G06F 3/044 324/686 |
| 2011/0048813 | A1* | 3/2011 | Yilmaz ................. G06F 3/044 178/18.06 |
| 2013/0088245 | A1* | 4/2013 | Sezginer ............... G03F 1/84 324/679 |
| 2014/0026652 | A1 | 1/2014 | Cummins et al. |

OTHER PUBLICATIONS

MD Nazmul Alam et al. Concrete Moisture Content Measurement Using Interdigitated Near-Field Sensors. IEEE Sensors Journal, vol. 10, No. 7, Jul. 1, 2010, pp. 1243-1248 [online], [retrieved on Sep. 24, 2015]. Retrieved from the Internet <URL: http://ieeexplore.ieee.org/stamp/stamp.jsp?arnumber=5473168> <DOI: 10.1109/JSEN.2010.2040175>.

* cited by examiner

AGRICULTURAL MOISTURE SENSOR WITH CO-PLANAR ELECTRODES

FIELD OF THE DISCLOSURE

The present disclosure relates to moisture sensors. More specifically, the present disclosure relates to moisture sensors on an agricultural machine for sensing moisture of an agricultural product.

BACKGROUND

Moisture sensors are used in agricultural harvesting equipment in order to obtain a measure of the moisture of the harvested product. Some current moisture sensors sense moisture by measuring the dielectric permittivity of the harvested product at one or more frequencies and then applying a calibration function in order to estimate the moisture, from the measured permittivity. Some such moisture sensors use a capacitive structure in which the harvested material forms the dielectric medium in the capacitive structure.

There are a variety of different types of moisture sensors, which have different geometries. One geometry involves the capacitive structure being formed as a parallel plate structure in which the material being measured passes between the plates of the capacitive structure, and forms the dielectric medium. One of the two plates is driven with an excitation voltage and the other plate senses current induced by an electric field passing through the capacitive structure. This type of structure works well for many materials, such as grains.

Some moisture sensors are also planar structures. The planar structures have a drive electrode to which an excitation voltage is applied, and the current passing through the drive electrode is also measured. The drive electrode sets up a fringing electric field that passes from it, out through the material being measured, and back to various grounded conductive surfaces in the same plane. The drive voltage and resulting current are measured and used to compute the permittivity of the measured material. These types of sensors can work better with soft, compressible material (such as hay, cotton and forage) that do not flow easily through a parallel plate structure.

The discussion above is merely provided for general background information and is not intended to be used as an aid in determining the scope of the claimed subject matter.

SUMMARY

A moisture sensor has a drive electrode and a separate sense electrode. Both electrodes have surfaces that face the sensed material and the surfaces are co-planar. The drive electrode receives an excitation signal and generates an electric field that produces a current in the sense electrode. The current is indicative of moisture in the sensed material.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

As mentioned in the background section, some moisture sensors have a planar structure. In such a structure, the electrodes are coplanar and the sensed material is placed into contact with the sensed material. The drive electrode receives an excitation signal and sets up a fringing electric field that passes through the sensed material. The fringing electric field passes back to the various grounded conductive surfaces in the plane of the electrode. The complex drive voltage and resulting complex current are measured and used to compute the permittivity of the material being tested.

Thus, in such planar structures, the current through the drive electrode is measured. A significant portion of this current, however, results from electric field flux lines that link to ground through media other than the material being measured. For instance, some of the electric field flux lines can link to ground through the air, through insulator components on the structure, and through other items.

This current is known as parasitic current and is caused by parasitic capacitive and conductive effects. The parasitic current can account for a large portion of the measured current (perhaps as much as 75% of the measured current), which results in a poor signal-to-noise ratio on the measured current.

In addition, the parasitic current is influenced by properties, especially temperature and humidity, of various materials, other than the material that is being measured. Some moisture sensors attempt to correct for the parasitic current in the calibration process. However, it can be very difficult to maintain an appropriate correction as the temperature and other conditions vary. This results in significant drift in the permittivity measurements.

Figure 1:
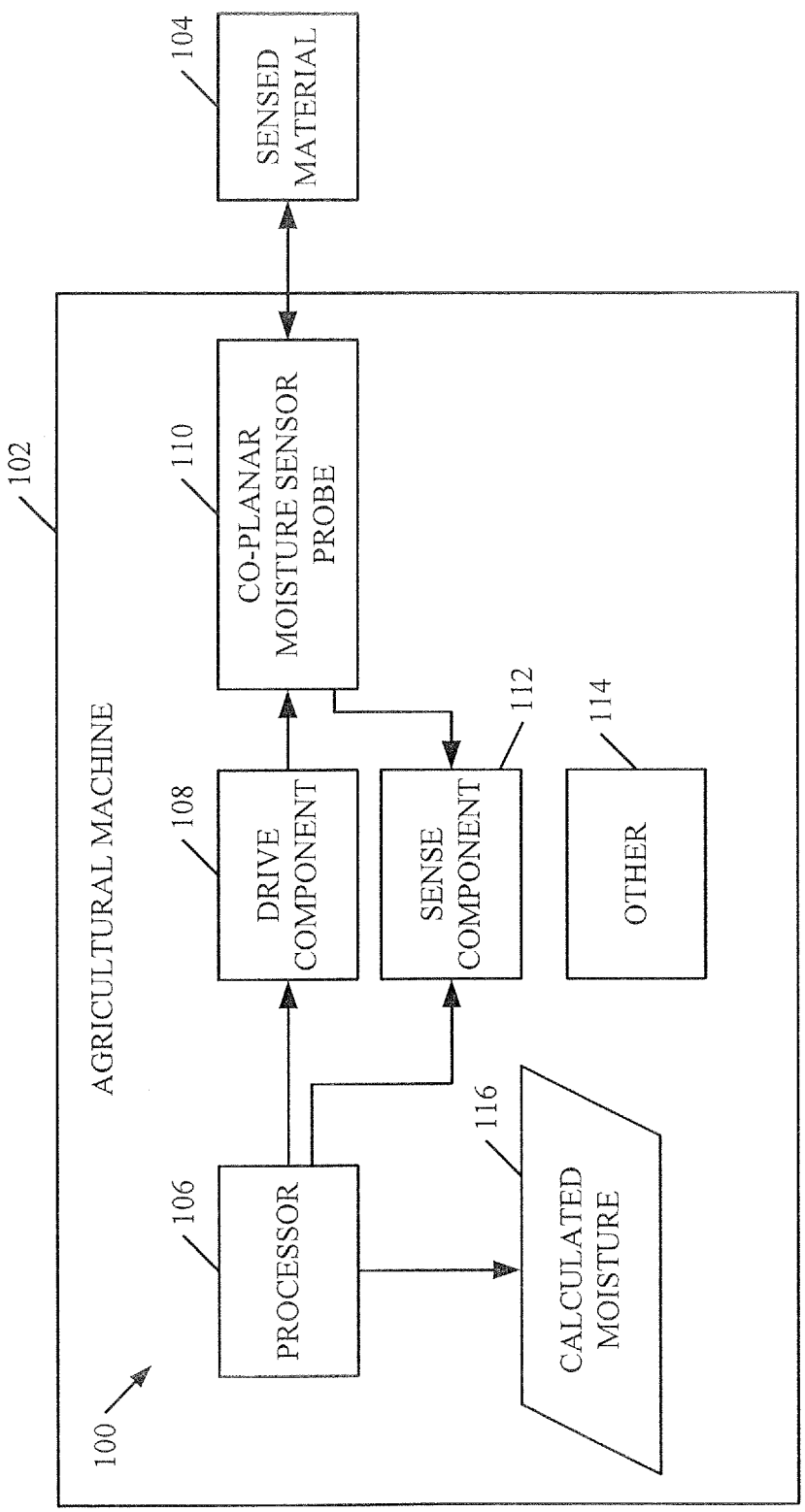
FIG. 1 is a block diagram of one embodiment of a moisture measuring system on an agricultural machine.

FIG. 1 shows one embodiment of a block diagram of a moisture sensing system 100 on an agricultural machine 102. Agricultural machine 102 can be a wide variety of different types of machines, such as a combine, a baler, a cotton harvester or a wide variety of other agricultural machines. Agricultural machine 102 illustratively comes into contact with sensed material 104 and has a conveying mechanism that conveys the material 104 through machine 102. As an example, the sensed material 104 can be material that is being harvested by agricultural machine 102. In an embodiment in which agricultural machine 102 is a combine, the sensed material 104 can be grain. When agricultural machine 102 is a baler, the sensed material 104 can be hay, cotton, or other baled material. These are examples only.

Moisture sensing system 100 illustratively includes processor 106, drive component 108, co-planar moisture sensor probe 110, sense component 112, and it can include other components 114 as well. Processor 106 is illustratively a computer processor with associated memory and timing circuitry, not separately shown. It controls drive component 108 to drive an electrode in co-planar moisture sensor probe 110. Sense component 112 illustratively senses a parameter (such as current) in one of the electrodes in co-planar moisture sensor probe 110 and provides that signal to processor 106. Processor 106 calculates a moisture value indicative of the moisture of sensed material 104. The calculated moisture is indicated by block 116 in FIG. 1.

Calculated moisture 116 can be used in a wide variety of different ways. For instance, it can be combined with a position signal in order to generate a moisture map. It can also be used in yield monitoring applications and to provide information to assist in making decisions about harvesting, storage, and future processing. It can be used in a wide variety of other ways as well.

Figure 2:
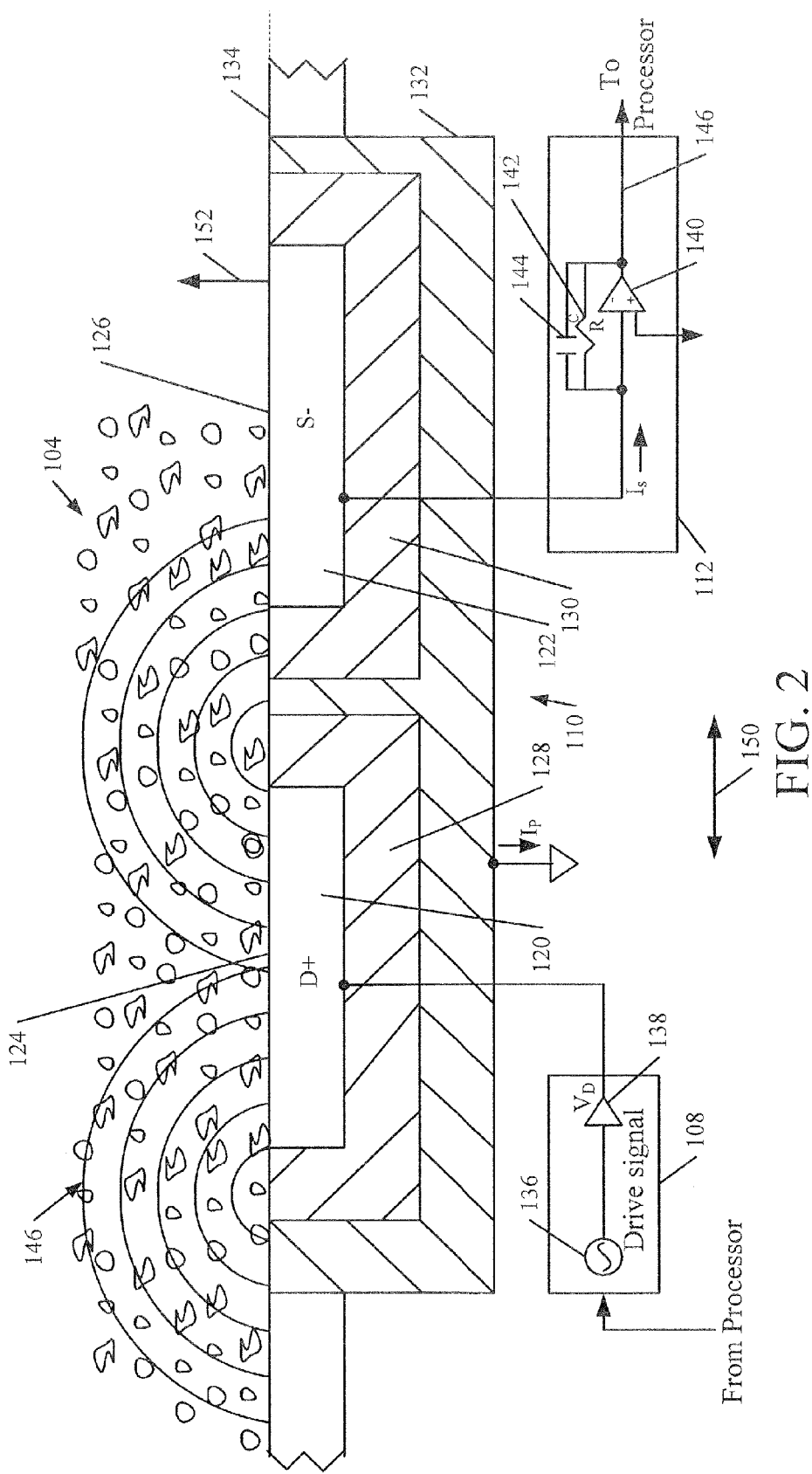
FIG. 2 is a partial schematic, partial sectional view of a portion of the moisture measuring system shown in FIG. 1.

FIG. 2 is a partial schematic, partial cross-sectional view of one embodiment of co-planar moisture sensor probe 110, drive component 108 and sense component 112. In the embodiment shown in FIG. 2, probe 110 includes a drive electrode 120 and a sense electrode 122. It will be appreciated that a plurality of different electrodes can be used and two are shown in the embodiment in FIG. 2 for the sake of example only.

Drive electrode 120 has a material facing surface 124 that is substantially co-planar with a material facing surface 126 of sense electrode 122. They are illustratively co-planar so that the material being measured 128 can come into contact with electrodes 120 and 122 on their co-planar surfaces, or at least come into close proximity to the surfaces. Each of the electrodes 120 and 122 illustratively has an insulator 128 and 130, respectively, disposed thereabout. Thus, electrodes 120 and 122 have insulators 128 and 130, respectively, encompassing all of their surfaces, except for the material facing surfaces 124 and 126.

Probe 110 also illustratively includes a ground electrode 132. Ground electrode 132 surrounds at least sense electrode 122 (and its insulator 130). It can surround both electrodes 120 and 122 and both insulators 128 and 130. However, it leaves exposed the material facing surfaces 124 and 126 of electrodes 120 and 122.

In the embodiment shown in FIG. 2, probe 110 is coupled to structural machine housing 134. This can be a housing of a combine, a baler, or another agricultural machine 102. For instance, where agricultural machine 102 is a combine, probe 110 can be mounted to housing 134 on the grain bypass of a clean grain elevator on the combine. In addition, it can be mounted on the bottom boot area of the clean grain elevator. Further, where the sensor is sensing moisture of other biomass material (such as material other than grain), it can be mounted to the rear of the rotor on a combine or on the residue hood adjacent the discharge beater of a combine. In addition, where agricultural machine 102 is a baler or cotton harvester, it can be mounted on an interior side wall of the bale chamber or harvester, or in other locations. These are given by way of example only, and the machine housing 134 can be another structural portion of an agricultural machine as well.

Drive component 108 illustratively includes a controllable oscillator 136. Oscilator 136 can be controlled by processor 106 to provide an alternating current (AC) drive signal to an operational amplifier 138 which, itself, provides an alternating current (AC) drive voltage $V_D$ at its output. Voltage $V_D$ is applied to drive electrode 120 as an excitation signal.

Sense component 112 illustratively includes a zero input impedance current sense amplifier 140 connected to an RC circuit formed by resistor 142 and capacitor 144. Sense component 112 is coupled to sense electrode 122 to receive sense current $I_S$ at its input. It provides, at its output, a signal 146 indicative of sense current $I_S$.

When the drive voltage $V_D$ is applied to drive electrode 120, electrode 120 illustratively produces a fringing electric field represented by electric field flux lines 146. The drive voltage $V_D$ can be provided at one or more frequencies in order to set up the electric field represented by flux lines 146. The electric field is set up by electrode 120, through the sensed material 104. The electric field links with all surrounding grounded surfaces in the plane of the material facing surfaces 124 and 126 of electrodes 120 and 122.

Sense electrode 126 is illustratively held at ground potential. The current induced in sense electrode 122 by the electric field passing through sense electrode 122 is referred to above as the sense current $I_S$.

Guard electrode 132 is also held at ground potential and inhibits any portion of the electric field that passes through the insulators 128 and 130, or paths other than through material 104, from reaching sense electrode 122. Instead, the parasitic current $I_P$ that is produced by flux lines through the insulator material or through other paths, other than the sensed material 104, is shorted to ground through guard electrode 132. It does not reach sense electrode 122. Thus, guard electrode 132 inhibits or blocks flux paths that do not pass solely through sensed material 104. They therefore do not contribute to the sensed current $I_S$.

Rather, the sensed current $I_S$, which is sensed in the sense electrode 122 (instead of the drive electrode 120) is induced only by the flux paths passing through the material being measured 104 and reaching sense electrode 122. The sense current $I_S$ is thus not influenced by parasitic flux paths through the insulators or directly to ground. All of that flux links with the grounded guard 132, so it does not affect sense current $I_S$.

Probe 110 is thus configured to measure only the permittivity of the sensed material 104 and is insensitive to characteristics of the probe structure (including, but not limited to, characteristics of the insulators 128 and 130 surrounding electrodes 120 and 122). By sensing current in the sense electrode 122, rather than the drive electrode 120, parasitic capacitive and conductive coupling between the drive electrode 120 and ground is substantially eliminated from the sensed current $I_S$. By maintaining both guard electrode 132 and the sense electrode 122 at ground potential, sensitivity to parasitic capacitance and conductance between the sense electrode 122 and the surrounding grounded structure is substantially eliminated as well.

It should be noted that other configurations for sensor probe 110 can be provided. For instance, if the drive electrode 120 and sense electrode 122 are moved further apart (such as in the direction indicated by arrow 150) or if they are moved closer together, this can affect the signal level of the sense current $I_S$. This is because the spacing between the two electrodes 120 and 122 will affect the depth of penetration of flux lines 146 into the sensed material 104. Moving them further apart will allow the flux lines 146 to penetrate more deeply into the sensed material 104 in the direction indicated by arrow 152. Moving them closer together will result in the flux lines 146 penetrating less deeply.

Figure 2A:
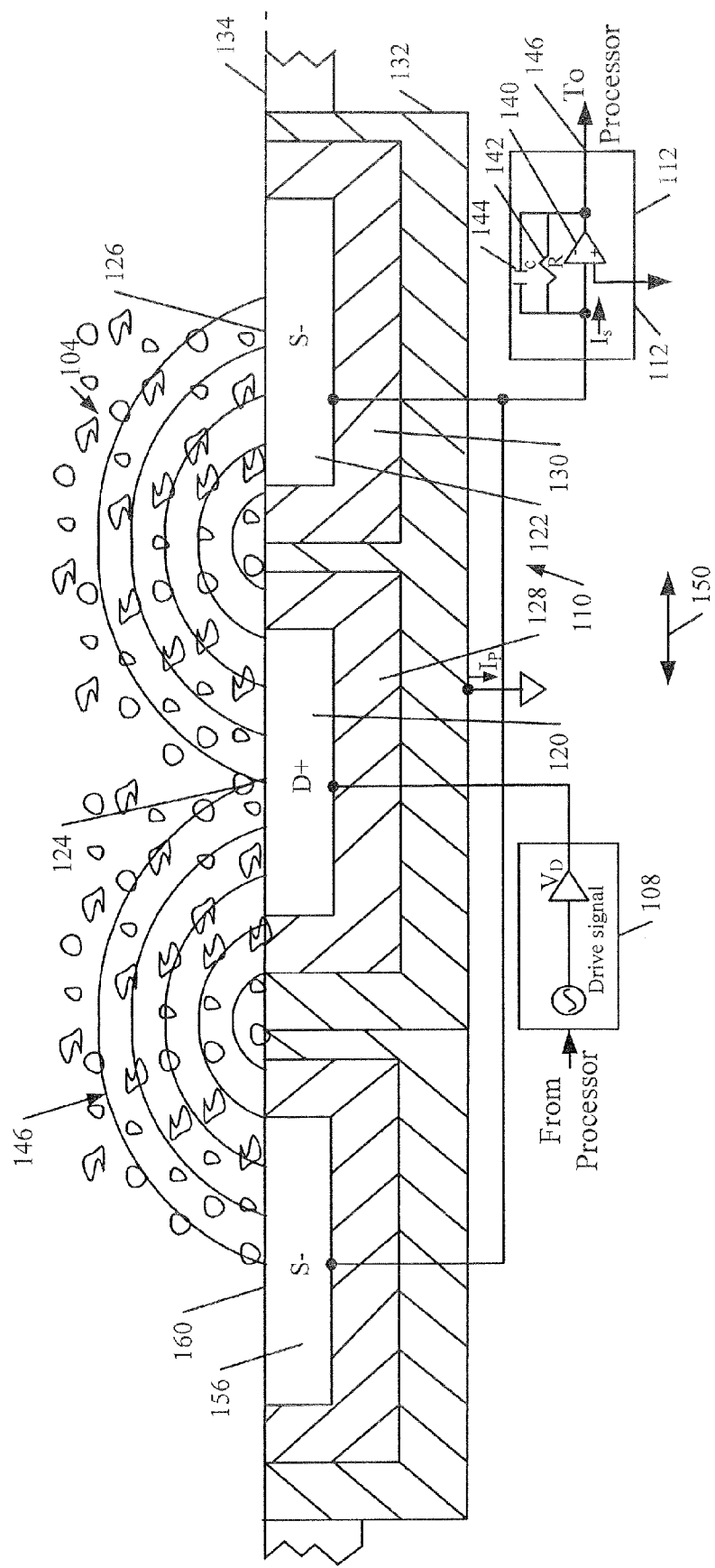
FIG. 2A is a partial schematic, partial sectional view of a portion of another embodiment of the moisture measuring system shown in FIG. 1.

FIG. 2A shows another exemplary configuration of co-planar moisture sensor probe 110. The embodiment shown in FIG. 2A is similar to that shown in FIG. 2, in some ways, and similar items are similarly numbered. It can be see, however, that in the embodiment shown in FIG. 2A, probe 110 not only includes drive electrode 120 and sense electrode 122, but it also includes a second sense electrode 156.

Sense electrode 156 also has an insulator 158 disposed thereabout. Like insulators 128 and 130, it is disposed about all surfaces of electrode 156 except the material facing surface 160 which is, itself, co-planar with the material facing surfaces 124 and 126 of electrodes 120 and 122. In addition, it can be seen that grounded guard electrode 132 also extends about all of the surfaces of sense electrode 156 (and insulator 158), except surface 160.

Thus, while the operation is similar to that shown in the embodiment of FIG. 2, the embodiment of FIG. 2A includes the additional sense electrode 156. Guard electrode 132 prevents flux lines 146 (other than those through the sensed material) from reaching sense electrode 156. Therefore, current induced by the flux lines 146 that reach sense electrodes 122 and 156 will be represented in sense current $I_S$.

It will be noted that other configurations can be used as well. For instance, multiple drive electrodes can be used with a single sense electrode, or there can be multiple drive electrodes and multiple sense electrodes. All of these various configurations are contemplated herein.

Figure 3:
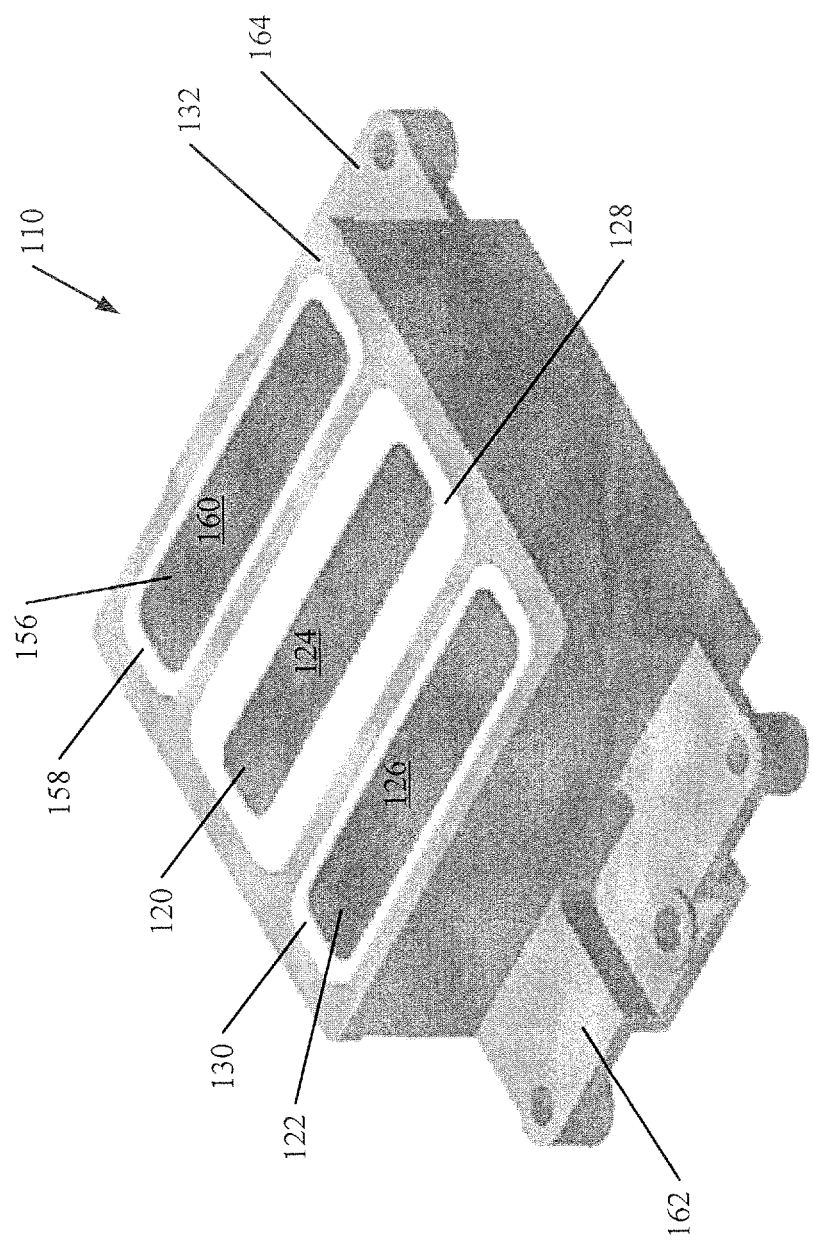
FIG. 3 is a perspective view of one embodiment of a moisture sensor probe.

FIG. 3 is a perspective, pictorial view of one embodiment of the sensor probe 110 shown in FIG. 2A. Similar items to those shown in FIG. 2A are similarly numbered in FIG. 3. In the embodiment shown in FIG. 3, probe 110 has a set of mounting structures 162 and 164 that can be used to mount probe 110 to machine housing 134. In one embodiment, the surfaces 124, 126 and 160 of electrodes 120, 122 and 156, respectively, are mounted flush with the machine housing 134. In another embodiment, however, they can protrude from the machine housing 134 in the direction of the material being measured 104 or they can be set back in the opposite direction. All of these embodiments are contemplated herein.

In addition, in one embodiment, grounded guard electrode 132 has through holes. The through holes receive electrical connection elements that connect a circuit board that includes drive component 108 and sense component 112 to the corresponding electrodes 120, 122 and 156. Of course, the particular configuration of the connections in sensor probe 110 can vary with the application. For instance, where probe 110 is mounted within a grain elevator, a clean grain tank, in the bale chamber of a baler, or on the spout of a combine or other harvester, the connections used to connect probe 110 to the machine housing 134 may vary. Also, the configuration may change, based upon the particular nature of the harvested material. When the harvested material is hay, cotton, or another relatively soft material, it may take one configuration (such as being flush with the machine housing 134). When it is a grain or other granular material, it may take another configuration, such as protruding slightly from the machine housing 134. Of course, these are given by way of example only, and the mounting configuration can vary in other ways as well.

Figure 4:
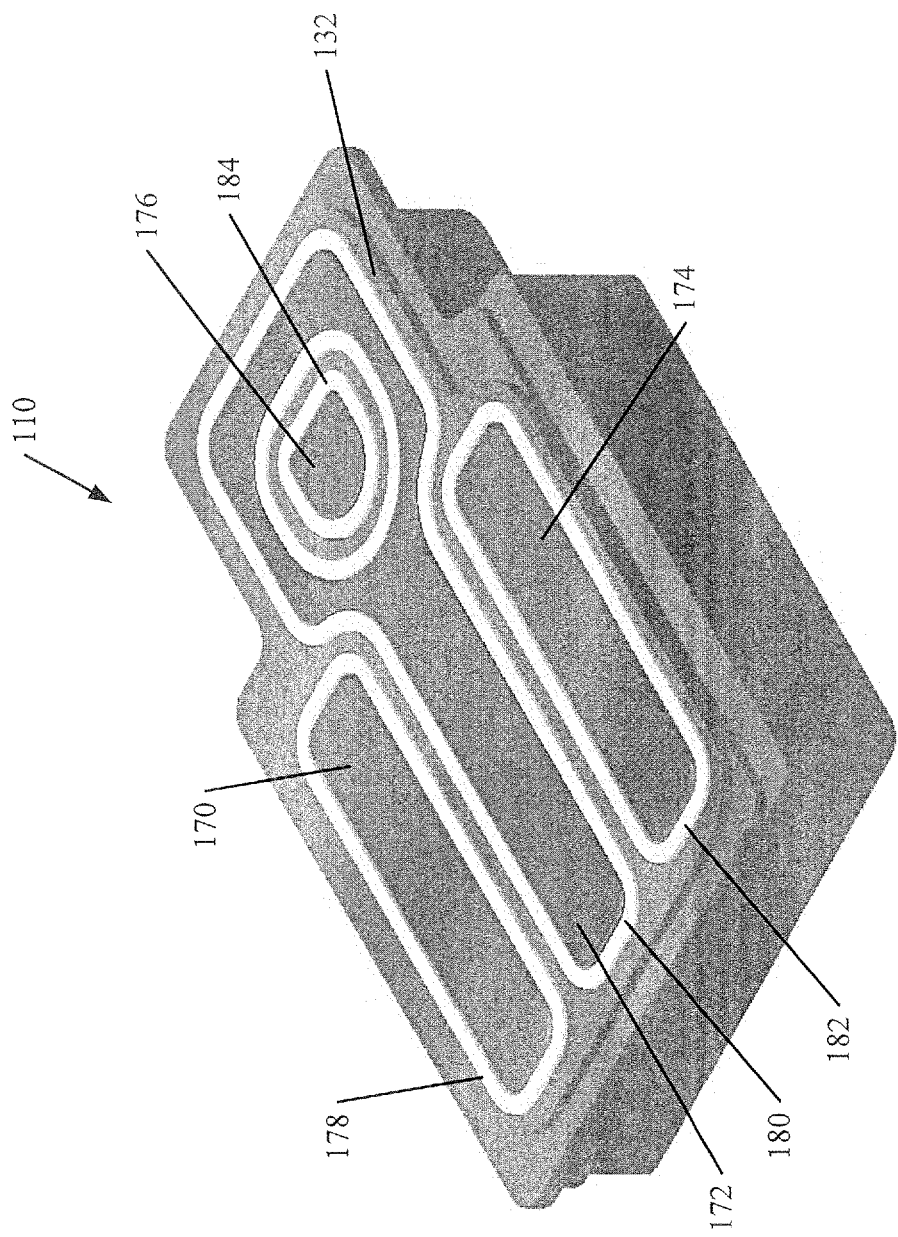
FIG. 4 is a perspective view of a second embodiment of a moisture sensor probe.

FIG. 4 shows another pictorial, perspective view of another embodiment of sensor probe 110. It can be seen that probe 110 shown in FIG. 4 includes four electrodes, 170, 172, 174 and 176. Each of the electrodes has a material facing surface that is seen in FIG. 4. All of the material facing surfaces are co-planar. Each of the electrodes is also surrounded by an insulating material 178, 180, 182 and 184, respectively. Further, the grounded guard 132 is disposed about all of the surfaces of the electrodes except their material facing surfaces (and about the insulators as well). In the embodiment shown in FIG. 4, some of the electrodes can be drive electrodes, while others can be sense electrodes. For instance, electrode 172 can be a drive electrode, while electrodes 170, 174 and 176 are sense electrodes. In another embodiment, electrode 176 is a fill sense electrode. It can be used when sensing grain. The probe is oriented so that it lies in a vertical plane and electrode 176 is higher than the other electrodes. In this orientation, when current above a minimum amount is sensed in electrode 176 the other electrodes are known to be completely covered with material (such as grain) and a valid permittivity measurement can be made. Of course, the drive electrodes and sense electrodes can be different as well. FIG. 4 shows that the particular geometrical configuration of the electrodes can take a wide variety of different forms.

It can thus be seen that by providing co-planar electrode surfaces on sensor probe 110, the complex drive voltage and resulting complex current can be measured and used to compute the permittivity of the sensed material 104. This, in turn, can be used to generate a measure of the moisture of material 104. The grounded guard electrode 132 that forms part of the probe structure is positioned relative to the sense electrodes so as to shield the sense electrodes from substantially all electric field flux that does not pass substantially only through the space where the sensed material 104 resides. Flux that is generated by the drive electrode and that passes through the insulator material or other things links with the grounded guard and is not sensed. With this configuration, the probe measures only the permittivity of the sensed material 104 and is relatively insensitive to characteristics of the probe structure (such as the insulators surrounding the electrodes). Further, by sensing currents in the sense electrode rather than in the drive electrode, parasitic capacitive and conductive coupling between the drive electrode and ground is substantially eliminated from the sensed current. Because the sense electrode is maintained at ground potential, sensitivity to parasitic capacitance and conductance between the sense electrode and the surrounding grounded structure is substantially eliminated as well.

It should also be noted that the different embodiments described herein can be combined in different ways. That is, parts of one or more embodiments can be combined with parts of one or more other embodiments. All of this is contemplated herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A moisture sensor, comprising:
 a drive component that generates a drive signal;
 a drive electrode coupled to the drive component and having a sensed material-facing surface, the drive electrode, when driven by the drive signal, generating an electric field;
 a sense electrode having a single sensed material-facing surface, the drive electrode and the sense electrode being structurally coupled to one another so the sensed material-facing surfaces of the drive electrode and the sense electrode are generally co-planar;
 a guard electrode disposed about the sense electrode, such that only the single sensed material-facing surface is exposed, wherein the guard electrode inhibits the electric field from reaching the sense electrode other than through the single sensed material-facing surface; and
 a sensing component coupled to the sense electrode and generating a sensing signal indicative of a current produced in the sense electrode by the electric field, generated by the drive electrode, reaching the sense electrode.

2. The moisture sensor of claim 1 wherein the guard electrode and the sense electrode are held at a reference voltage potential.

3. The moisture sensor of claim 2 wherein the guard electrode is disposed to form a guard about the sense electrode, and to define an opening to expose the signal sensed material-facing surface to direct contact with the sensed material.

4. The moisture sensor of claim 3 wherein the guard electrode is disposed about substantially all surfaces of the sense electrode other than the single sensed material-facing surface.

5. The moisture sensor of claim 3 and further comprising:
an insulator disposed between the sense electrode and the guard electrode.

6. The moisture sensor of claim 3 and further comprising:
an insulator disposed between the drive electrode and the guard electrode.

7. The moisture sensor of claim 2 wherein the sense component comprises:
a current sense amplifier having an input held at the reference voltage potential and receiving, at the input, the current produced in the sense electrode.

8. The moisture sensor of claim 7 wherein the drive component comprises:
an alternating current (AC) component generating the drive signal as an AC excitation signal.

9. The moisture sensor of claim 8 and further comprising:
a computer processor that measures the AC excitation signal and the sensing signal and determines a moisture level of material proximate the sensed material-facing surfaces of the drive electrode and the sense electrode, based on the AC excitation signal and the sensing signal.

10. The moisture sensor of claim 1, wherein the single sensed material-facing surface is configured to contact an agricultural material receiving area of an agricultural machine, and wherein the sensing component is configured to generate a sensor signal indicative of a moisture content of agricultural material flowing through the agricultural material receiving area.

11. The moisture sensor of claim 10, wherein single sensed material-facing surface is configured to directly contact the agricultural material within the agricultural material receiving area.

12. An agricultural machine that transports agricultural material, comprising:
a material conveying mechanism defining a material area through which the agricultural material passes; and
a sensor probe comprising:
a drive electrode having a material facing surface facing the material area of the material conveying mechanism;
a sense electrode having a material facing surface that is co-planar with the material facing surface of the drive electrode, wherein the drive electrode is configured to receive a drive signal and generate an electric field that produces a current in the sense electrode; and
a guard electrode disposed about the sense electrode to inhibit the electrical field from reaching the sense electrode other than through the material area, and the sensor probe being mounted relative to the material conveying mechanism to generate a moisture sensor signal, based on the current produced in the sense electrode, indicative of moisture in the agricultural material passing through the material area of the material conveying mechanism.

13. The agricultural machine of claim 12 wherein the sense electrode and the guard electrode are held at a reference voltage potential.

14. The agricultural machine of claim 13 and further comprising:
an insulator separating the drive electrode, the sense electrode and the guard electrode.

15. The agricultural machine of claim 13 wherein the material conveying mechanism comprises a bale chamber of a baler.

16. The agricultural machine of claim 15 wherein the sensor probe is mounted to a side wall of the bale chamber so the material facing surfaces of the drive electrode and the sense electrode face an interior of the bale chamber.

17. The agricultural machine of claim 13 wherein the material conveying mechanism comprises:
a grain conveying mechanism of a combine.

18. The agricultural machine of claim 13 wherein the material conveying mechanism comprises:
a residue discharge portion of a combine.

19. A moisture sensor probe, comprising:
a drive electrode configured to receive an excitation signal and generate an electric field based on the excitation signal, the drive electrode including a sensed material facing electrode surface;
a sense electrode, having a sensed material facing surface that is coplanar with the sensed material facing surface of the drive electrode, and positioned relative to the drive electrode so the electric field produces a current in the sense electrode; and
a guard electrode having a non-coplanar portion that is substantially non-coplanar with the sensed material facing surface, and being disposed about substantially all surfaces of the sense electrode other than the sensed material facing surface such that it substantially eliminates contributions to a flow of the electric field through the sense electrode other than through the sensed material facing surface of the sense electrode.

20. The moisture sensor probe of claim 19 wherein the sense electrode and the guard electrode are held at a reference voltage potential.

21. The moisture sensor probe of claim 19 and further comprising: an insulator separating the sense electrode and the drive electrode.

22. The moisture sensor probe of claim 19 and further comprising: an insulator separating the sense electrode and the guard electrode.

23. The moisture sensor probe of claim 19, wherein the sensed material facing surface is configured to contact an agricultural material receiving area of an agricultural machine, and wherein the moisture sensor probe is configured to generate a sensor signal indicative of a moisture content of agricultural material flowing through the agricultural material receiving area.

* * * * *

UNITED STATES PATENT AND TRADEMARK OFFICE
CERTIFICATE OF CORRECTION

PATENT NO. : 9,494,538 B2
APPLICATION NO. : 14/245069
DATED : November 15, 2016
INVENTOR(S) : Kozicki et al.

It is certified that error appears in the above-identified patent and that said Letters Patent is hereby corrected as shown below:

On the Title Page

Item (72) please correct the inventor(s) names as follows:

[Andrze J Kozicki] – Andrzej Kozicki

[Jefrey S. Wigdahl] – Jeffrey S. Wigdahl

Signed and Sealed this
Seventh Day of February, 2017

Michelle K. Lee
*Director of the United States Patent and Trademark Office*